United States Patent
Arisoy et al.

(10) Patent No.: US 9,542,525 B2
(45) Date of Patent: Jan. 10, 2017

(54) ADDITIVE SMOOTHING OF SHARP CONCAVE EDGES ON DESIGNED 3D PRINTABLE POLYGONAL MESH MODELS

(71) Applicant: Siemens Product Lifecycle Management Software Inc., Plano, TX (US)

(72) Inventors: Erhan Arisoy, Pittsburgh, PA (US); Suraj Ravi Musuvathy, Glenmont, NY (US); Livio Dalloro, Princeton, NJ (US)

(73) Assignee: Siemens Product Lifecycle Management Software Inc., Plano, TX (US)

( * ) Notice: Subject to any disclaimer, the term of this patent is extended or adjusted under 35 U.S.C. 154(b) by 385 days.

(21) Appl. No.: 14/312,794

(22) Filed: Jun. 24, 2014

(65) Prior Publication Data
US 2015/0370958 A1 Dec. 24, 2015

(51) Int. Cl.
| | |
|---|---|
| *G06F 17/50* | (2006.01) |
| *A61F 2/30* | (2006.01) |
| *G06T 19/20* | (2011.01) |
| *B33Y 50/00* | (2015.01) |
| *G06T 17/20* | (2006.01) |

(52) U.S. Cl.
CPC ....... *G06F 17/5086* (2013.01); *A61F 2/30942* (2013.01); *B33Y 50/00* (2014.12);
(Continued)

(58) Field of Classification Search
CPC ........... G06T 17/205; G06T 2219/2021; G06T 19/20; G06T 2210/41; A61F 2/30942; B33Y 50/00; B33Y 10/00; B33Y 50/02; G06F 17/5086
See application file for complete search history.

(56) References Cited

U.S. PATENT DOCUMENTS

| | | | |
|---|---|---|---|
| 2006/0094951 A1* | 5/2006 | Dean | G06F 19/3437 600/407 |
| 2012/0209394 A1 | 8/2012 | Bojarski | |

FOREIGN PATENT DOCUMENTS

| | | |
|---|---|---|
| WO | 03030787 A1 | 4/2003 |
| WO | 2004110309 A2 | 12/2004 |

(Continued)

OTHER PUBLICATIONS

PCT International Search Report mailed Oct. 13, 2015 for corresponding PCT Application No. PCT/US2015/036623 filed Jun. 19, 2015 (20 pages).
(Continued)

*Primary Examiner* — Kenneth M Lo
*Assistant Examiner* — Derrick Boateng

(57) ABSTRACT

A method for designing a personalized medical device includes receiving a template design of a medical device. An image including a patient anatomical geometry is acquired. The template design is combined with the image including the patient anatomical geometry to create a custom medical device design. A region of interest encompassing the sharp concave edge is automatically identified within the custom medical device design using one or more seed points received from a user. Surface smoothing of the custom medical device design is performed within the region of interest to bolster a thickness of the custom medical device design. A 3D-printable model is obtained from the surface smoothed custom medical device design.

20 Claims, 8 Drawing Sheets

(52) U.S. Cl.
CPC ............ *G06T 17/205* (2013.01); *G06T 19/20* (2013.01); *G06T 2210/41* (2013.01); *G06T 2219/2021* (2013.01)

(56) References Cited

FOREIGN PATENT DOCUMENTS

| | | |
|---|---|---|
| WO | 2012027150 A2 | 3/2012 |
| WO | 2013170872 A1 | 11/2013 |

OTHER PUBLICATIONS

Kronman Achia et al: "Image Segmentation Errors Correction by Mesh Segmentation and Deformation", Sep. 22, 2013 (Sep. 22, 2013), Advances in Communication Networking : 20th EUNICE/IFIP EG 6.2, 6.6 International Workshop, Rennes, France, Sep. 1-5, 2014, Revised Selected Papers; Lecture Notes in Computer Science , ISSN 1611-3349], Springer Verlag, DE, pp. 206-213, XP047042070; 2013.

\* cited by examiner

ADDITIVE SMOOTHING OF SHARP CONCAVE EDGES ON DESIGNED 3D PRINTABLE POLYGONAL MESH MODELS

TECHNICAL FIELD

The present disclosure relates to polygon mesh models and, more specifically, to additive smoothing of sharp concave edges on designed 3D printable polygonal mesh models.

DISCUSSION OF THE RELATED ART

Personalized medical devices are devices that have been custom-made to conform to the anatomy of a particular patient. Personalized medical devices may have a wide variety of uses and may be designed for use inside and outside the patient's body as tools, hardware, implants, prosthetics, etc.

This technology is presently used in and has great potential to be used in medical fields such as orthopedics, dentistry, cardiology, audiology, podiatry, surgery, etc.

The growing availability of 3D printers has made on-site fabrication of personalized medical devices more readily accessible. The process for fabricating personalized medical devices often includes a technician manually editing a computer aided design (CAD) of a medical device to conform to the anatomy of a particular patient. After the CAD has been so edited, it may be sent to a 3D printer, which may be able to quickly create the device in accordance with the edited design, without having to wait what could otherwise be weeks.

SUMMARY

A method for designing a personalized medical device includes receiving a template design of a medical device. An image including a patient anatomical geometry is acquired. The received template design of the medical device is combined with the acquired image including the patient anatomical geometry to create a custom medical device design. The combined image is displayed to a user. One or more seed points indicative of a location of a sharp concave edge present within the custom medical device design is received from a user. A region of interest encompassing the sharp concave edge is automatically identified within the custom medical device design using the one or more seed points received from the user. Surface smoothing of the custom medical device design is performed within the region of interest to bolster a thickness of the custom medical device design within the region of interest. A model is obtained from the surface smoothed custom medical device design.

The received template design of the medical device may be a three-dimensional polygonal mesh model.

The received template design of the medical device is a computer aided design (CAD) model.

A computed tomography (CT) scanner may be used to acquire the image including the patient's anatomical geometry and the acquired image is a CT scan.

One or more Boolean operators may be used to combine the received template design of the medical device with the acquired image including the patient anatomical geometry.

The user may provide two seed points indicative of the location of the sharp concave edge including a first seed point located on one side of the sharp concave edge and a second seed point located on an opposite side of the sharp concave edge.

Automatically identifying the region of interest encompassing the sharp concave edge may include identifying shortest paths from the first seed point to a top and bottom boundary of the region of interest, identifying shortest paths from the second seed point to a top and bottom boundary of the region of interest, and identifying the region of interest as an area between the shortest paths of the first seed point and the shortest paths of the second seed point.

After the region of interest is automatically identified, the user may be provided with an opportunity to modify the region of interest either by adding/removing sections from the region of interest or by selecting one or more replacement seed points.

Performing surface smoothing of the custom medical device design within the region of interest may include performing one or more mesh fairing techniques.

Performing surface smoothing of the custom medical device design within the region of interest may include performing one or more edge blending techniques.

Performing surface smoothing of the custom medical device design within the region of interest may include performing one or more sphere fitting techniques.

Performing surface smoothing of the custom medical device design within the region of interest may include iteratively performing additive blending and sphere fitting.

Performing surface smoothing of the custom medical device design within the region of interest may include performing inflation of concave vertices.

Performing surface smoothing of the custom medical device design within the region of interest may include applying anisotropic discrete filter formulation that uses local principal curvature values to detect local sharp regions and utilizing a smoothing algorithm to apply different amounts of energy minimization to different local regions within the region of interest.

Performing surface smoothing of the custom medical device design within the region of interest may include performing mean curvature flow-based smoothing to preserve local features.

Performing surface smoothing of the custom medical device design within the region of interest may include applying bilateral filters to discrete surfaces of the custom medical device design to denoise surfaces thereof while preserving sharp features.

The model obtained from the surface smoothed custom medical device design may be a 3D-printable mesh model.

The model obtained from the surface smoothed custom medical device design may be 3D printed.

A method for fabricating a personalized medical device includes receiving a template design of a medical device. An image including a patient anatomical geometry may be acquired. The received template design of the medical device is combined with the acquired image including the patient anatomical geometry to create a custom medical device design. A region of interest encompassing the sharp concave edge is identified within the custom medical device design using one or more seed points received from a user. Surface smoothing of the custom medical device design is performed within the region of interest to bolster a thickness of the custom medical device design within the region of interest. The surface-smoothed custom medical device design is 3D printed.

A computer system includes a processor and a non-transitory, tangible, program storage medium, readable by the computer system, embodying a program of instructions executable by the processor to perform method steps for designing a personalized medical device. The method includes receiving a template design of a medical device. An image including a patient anatomical geometry is acquired. The received template design of the medical device is combined with the acquired image including the patient anatomical geometry to create a custom medical device design. A region of interest encompassing the sharp concave edge is identified within the custom medical device design using one or more seed points received from a user. Surface smoothing of the custom medical device design is performed within the region of interest to bolster a thickness of the custom medical device design within the region of interest.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

Figure 1:
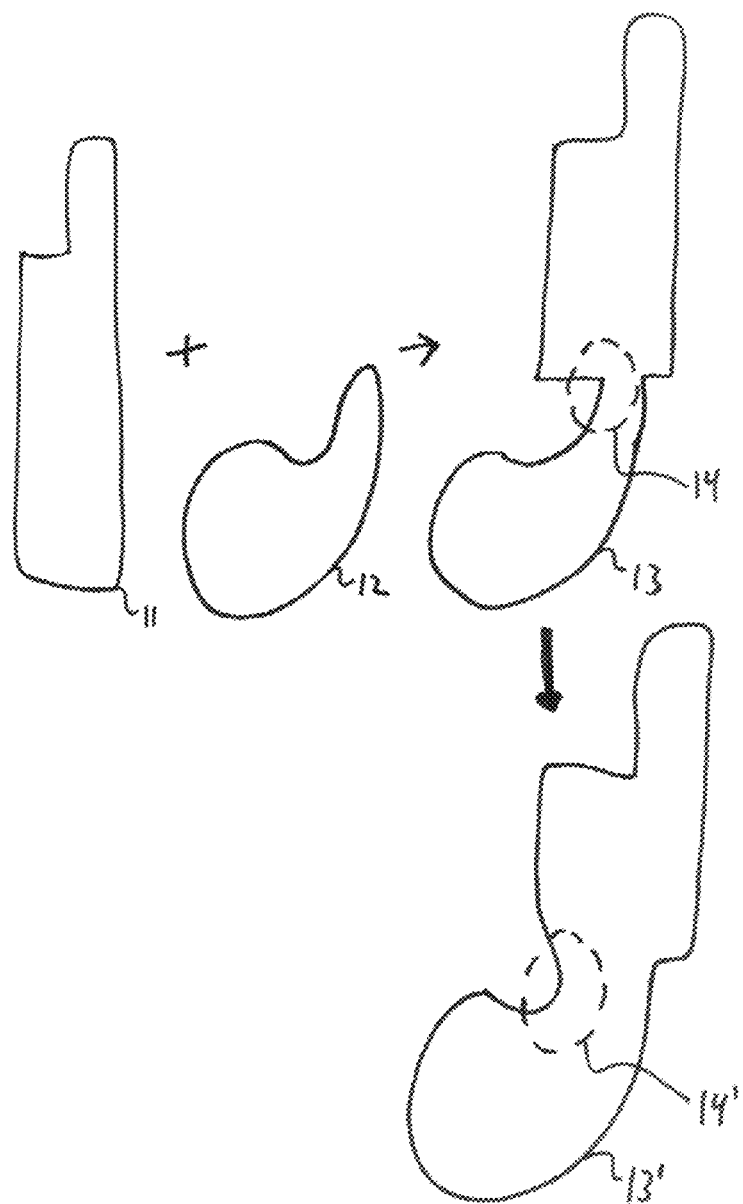
FIG. 1 is a diagram illustrating the combination of the acquired patient geometry and the designed model in accordance with exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiment of the present invention seek to provide systems and methods for designing and manufacturing personalized medical devices. These personalized medical devices may be fabricated from CAD models, which may be 3D polygonal mesh models. A template model may be modified in accordance with the exact anatomical geometry of a patient and this modified model may then be fabricated using a 3D printer.

The anatomical geometry of a patient may be acquired using a medical imaging device such as a computed tomography (CT) scanner, magnetic resonance imager (MRI), or from multiple 2D images acquired from different angles using a C-arm mounted x-ray device. As personalized medical devices may also be placed outside of the patient's body, for example, as a cast for setting a broken arm, imaging devices such as stereoscopic digital camera, 3D laser scanners, or the like may be used acquire 3D patient geometry.

The anatomical geometry may thereafter be incorporated into a designed CAD model for the medical device being constructed. This combining may be performed using Boolean operations or other available means.

However, the use of Boolean operations to combine the acquired patient geometry with the designed model may lead to sharp concave edges, for example, at the junction of the two shapes. FIG. 1 is a diagram illustrating the combination of the acquired patient geometry and the designed model in accordance with exemplary embodiments of the present invention. In this figure, shape 11 represents the designed model. While it is to be understood that exemplary embodiments of the present invention contemplate the use of 3D shapes, and in particular, a 3D designed model, the shapes of FIG. 1 are illustrated in 2D for the purpose of providing a simple and clear explanation and it is to be understood that, while this approach may indeed be performed with 2D shapes, exemplary embodiments of the present invention may be performed with 3D shapes.

As can be seen in FIG. 1, the designed model 11 may have a fairly regular shape with straight lines and deliberate curves. This stands in contrast to shape 12, which represents a segment of anatomical geometry that has been acquired, for example, by way of obtaining a digital scan of the patient. The anatomical geometry 12 may have a more irregular shape with many curves.

Even where neither the anatomical geometry 12 nor the designed model 11 has sharp edges, the combined 3D polygonal mesh model, represented as shape 13, may indeed have one or more sharp and/or concave edges, especially where the combination is performed using a Boolean operator. Area 14 highlights one such sharp/concave edge.

Sharp and/or concave edges in medical devices may pose a number of challenges. For example, the structural integrity of the medical device, during fabrication or use, may be compromised. Indeed a sharp/concave edge may create a narrow section in the medical device that may act as a stress point during manufacturing and/or use and may lead to the device breaking apart at the stress point. This may be of particular concern during the process of 3D printing, in which the structure being fabricated may come under stress.

Exemplary embodiments of the present invention seek to modify the combined 3D polygonal mesh model in such a way as to smooth out and bolster the sharp/concave edges thereof. As smoothing of the shape may either lead to the increase or reduction of the device thickness at the site of the concavity, exemplary embodiments of the present invention seek to increase the device thickness at these sections by adding additional material to the device as the region is smoothed. In this way, the device is said to be bolstered. As can be seen in FIG. 1, the smoothed and bolstered 3D polygonal mesh model 13' no longer appears vulnerable to cracking and breakage in area 14'. The 3D polygonal mesh model, so modified, may then be 3D printed and utilized with a reduced risk of breakage.

Exemplary embodiments of the present invention may use one or more mesh fairing techniques to smooth and bolster the sharp/concave regions. Mesh fairing may be preferable to edge blending techniques, which may also be used to smooth transitions, as edge blending may be less suitable for 3D polygonal models. However, as some edge blending techniques may be adapted for 3D polygonal models, exemplary embodiments of the present invention may alternatively or additionally use edge blending techniques to smooth and bolster the sharp/concave regions.

Mesh fairing techniques may be based on geometric flows. Such techniques may define mesh smoothing problems as an energy minimization problem such as curvature, gradient, surface area or volume. One example of a mesh fairing technique based on geometric flows is the Laplacian based smoothing algorithm. In its simplest formulation, Laplacian smoothing repositions vertices of the original mesh to the barycenter of their one ring neighbors. The integral of the sum of the maximal and minimal principal curvatures may be used as an energy minimization. According to another example, a spring model may be used to minimize variation of curvature energy for generating a more blobby looking geometry.

However, as these mesh fairing techniques may result in excessive energy loss and loss of important fine detail of the original geometries such as sharp edges or high curvature regions, exemplary embodiments of the present invention may utilize an anisotropic discrete filter formulation that uses local principal curvature values to detect local sharp regions. Based on these detection results, the smoothing algorithm used may apply different amounts of minimization to different local regions. Mean curvature flow based smoothing may also be used to better preserve local features.

Other examples of mesh fairing techniques that may be used are spectral methods, which may be adapted from the image processing domain. Here bilateral filters may be applied to discrete surfaces of the mesh model to denoise surfaces while preserving sharp features. The efficient computation of eigenvectors of meshes with a number of vertices greater than a couple of thousand may be achieved by calculating a Fourier like transformation on meshes using Manifold Harmonic Basis functions and then applying band pass filtering on this transformation.

Other examples of mesh fairing techniques that may be used are optimization based techniques which provide a certain smoothness quality while minimizing different energy functions. Here, Laplacian smoothing may be combined with optimization to increase mesh quality. For example, Laplacian mesh optimization based on least square meshes where the smoothing is not applied iteratively, but rather is calculated in one step by solving a linear system of equations. This formulation may preserve Laplacian coordinates and introduce positional soft constraints to preserve local features.

Regardless of the approach used, exemplary embodiments of the present invention may achieve mesh fairing or increased quality based on repositioning the vertices of the original object.

Figure 2:
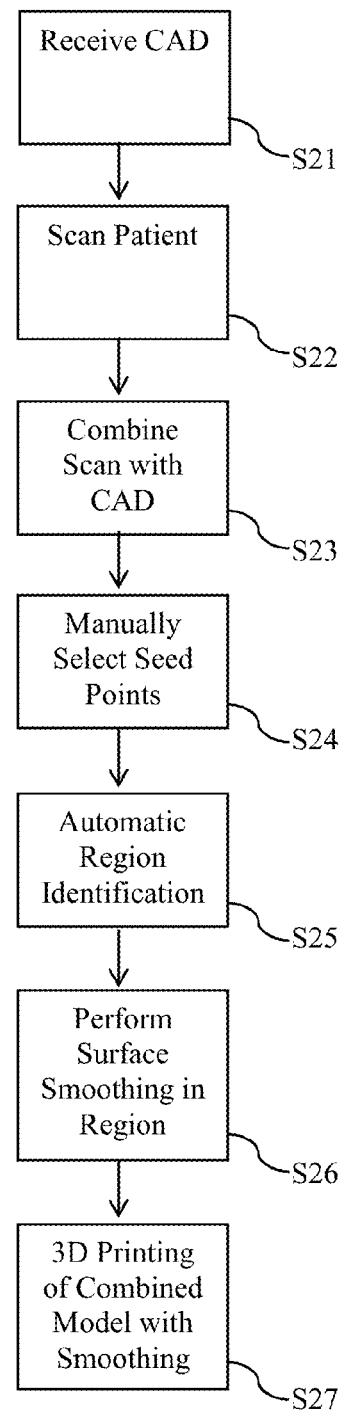
FIG. 2 is a flow chart illustrating an approach for creating personalized medical devices in accordance with exemplary embodiments of the present invention.
Figure 3:
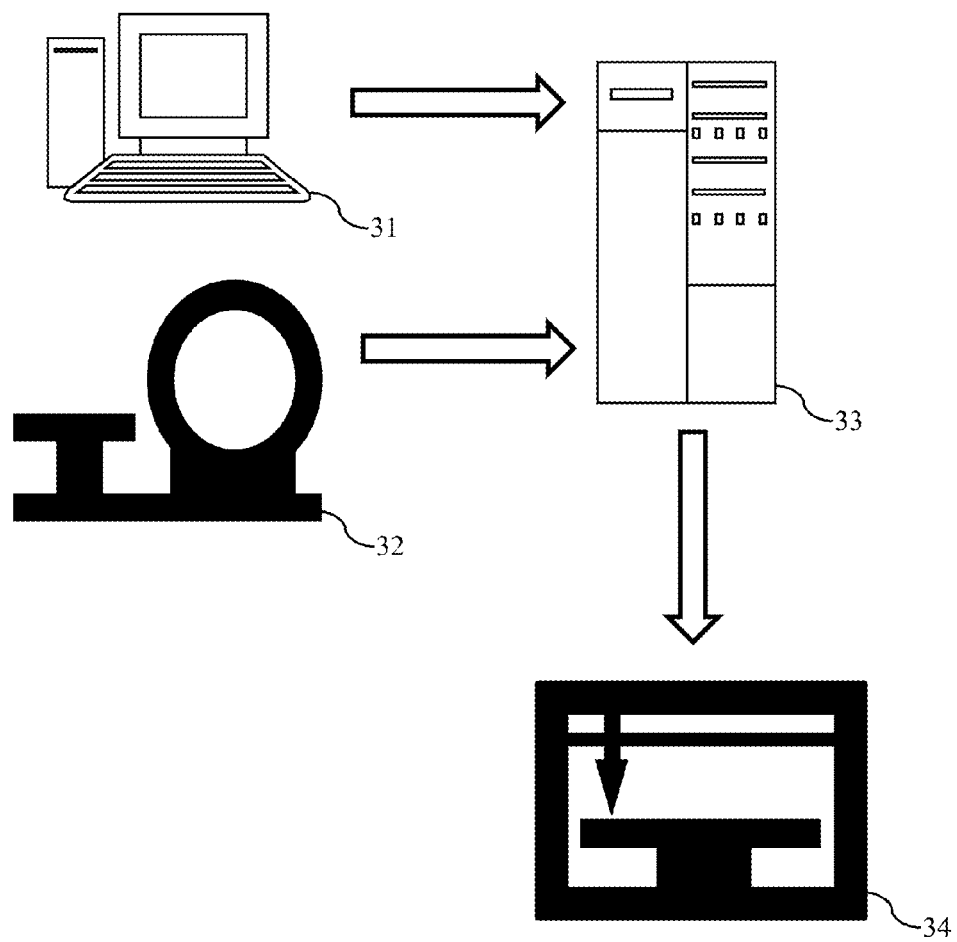
FIG. 3 is a schematic diagram illustrating a system for creating personalized medical devices in accordance with exemplary embodiments of the present invention.

FIG. 2 is a flow chart illustrating an approach for creating personalized medical devices in accordance with exemplary embodiments of the present invention. FIG. 3 is a schematic diagram illustrating a system for creating personalized medical devices in accordance with exemplary embodiments of the present invention. While the described approaches are framed with respect to creating personalize medical devices, it is to be understood that the techniques described herein for removing sharp/concave edges in polygonal mesh models may be applied more generally to a wide variety of uses.

First, a computer aided design (CAD) may be received (Step S21). The CAD may represent a design for a medical device that is generic with respect to a particular patient. The CAD may be manually designed by a designer at a computer workstation 31 and stored in a database for subsequent use. The CAD may be a polygonal mesh model expressing a generic shape for the medical device.

A patient may be scanned to acquire an anatomical geometry of the patient (Step S22). As discussed above, a CT scanner may be used for this purpose. Thereafter, the received CAD and the patient's scan may be combined to produce a combined 3D polygonal mesh model representing an implementation of the medical device that has been customized for the particular patient's anatomical geometry (Step S23). The combination of the CAD and the patient's scan may be performed using a graphics processing computer 33 that may be the same computer or a different computer from the computer workstation 31 used to generate the CAD file.

Figure 4A:
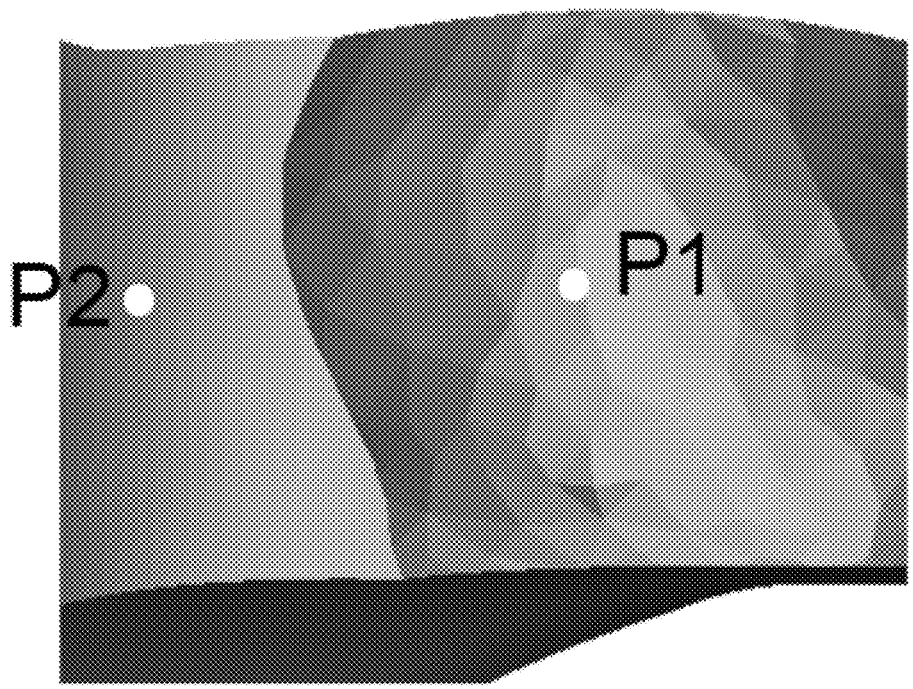
FIGS. 4A-4D are graphical depictions illustrating a portion of a 3D polygonal model and an approach for identifying a sharp/concave edge section thereof in accordance with exemplary embodiments of the present invention.
Figure 4B:
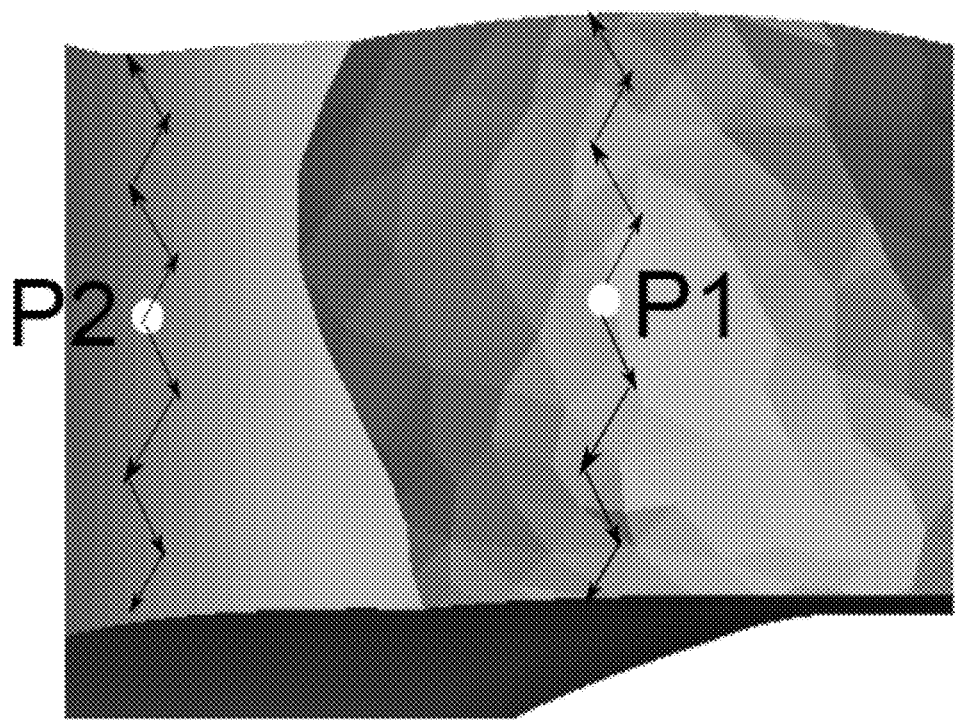
Figure 4C:
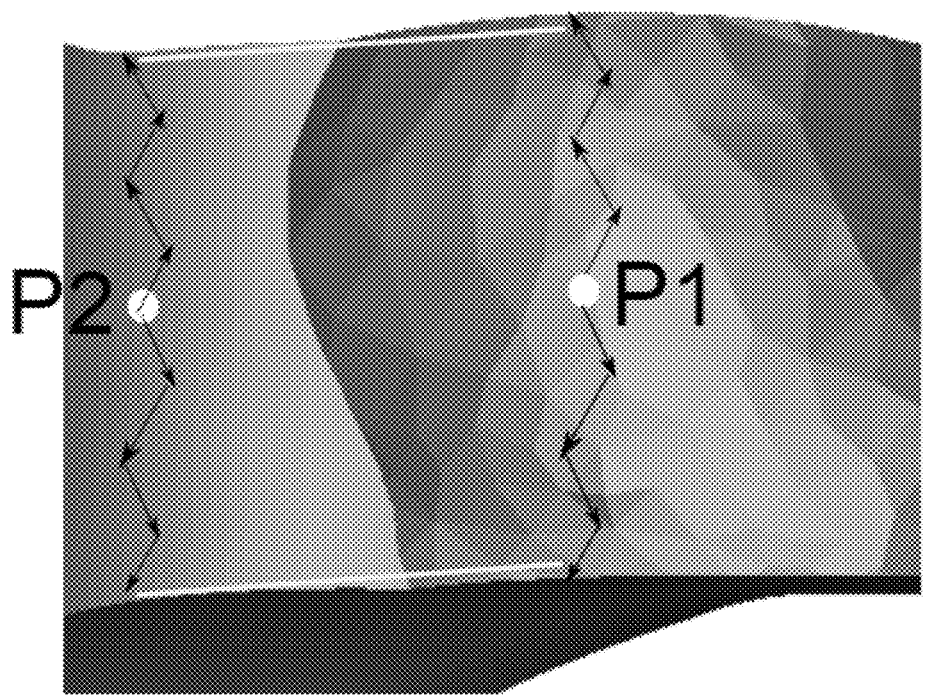
Figure 4D:
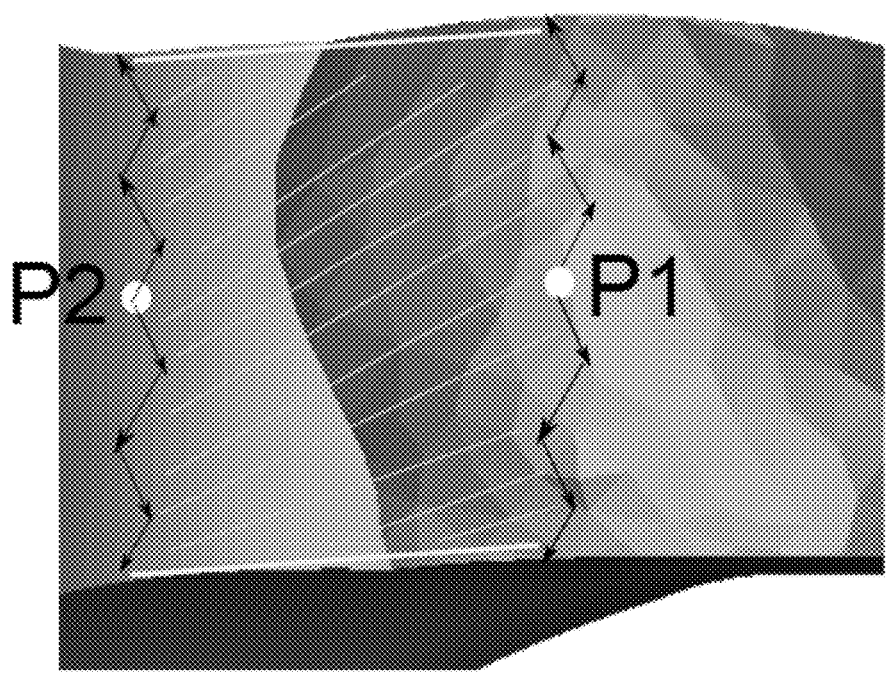

The CAD and the patient scan may be combined using a Boolean modeling operation. Thereafter, as described above, one or more sharp/concave edges may be present in the combined model. A user may then be presented with the combined model and prompted to select seed points (Step S24). FIGS. 4A-4C are graphical depictions illustrating a portion of a 3D polygonal model and an approach for identifying a sharp/concave edge section thereof in accordance with exemplary embodiments of the present invention. As can be seen in FIG. 4A, a user may identify two seed points, a first seed point P1 located on one side of a concave edge region and a second seed point P2 located on an opposite side of the concave edge region. Then, as may be seen in FIG. 4B, shortest paths between the seed points and the boundaries may be automatically determined (shortest paths illustrated with arrows). Then, as may be seen in FIG. 4C, shortest paths between the corresponding ends of the two shortest paths may be automatically determined (paths between corresponding ends illustrated with white lines). Thereafter, as may be seen in FIG. 4D, the region of the sharp/concave edge may be automatically identified (Step S25) as the area within the shortest paths of FIG. 4B and the paths between corresponding ends of FIG. 4C (detected region illustrated with diagonal white lines).

Accordingly, the region of interest representing the region in which the sharp/concave edge is found, may be automatically identified (Step S25) by path tracing and region growing, as discussed above. For example, as shown in FIGS. 4A-4D, paths are traced from the user selected points parallel to the edge and until sharp boundary edges are reached. The region of interest may then be filled-in between the traced paths and the sharp edges. At this stage, a user may be prompted with the opportunity to edit the automatically identified region, for example, by adding or removing polygons or by re-initiating the region detection by editing one or both of the initial seed points.

Surface smoothing may then be performed within the automatically identified area of interest (Step S26). Surface smoothing may be performed using additive edge blending in accordance with exemplary embodiments of the present invention. In additive edge blending, the triangles labeled as the concave region may be modified using a combination of local sphere fitting and smoothing to the vertices in the region of interest.

In performing local sphere fitting, a vertex may be modified such that it lies approximately on a sphere fitted to its local neighborhood. The vertex position may therefore be found to satisfy each of the following three equations:

$$P_{xi} = C_{xlocalsphere} + r \times N_{xi}$$

$$P_{yi} = C_{ylocalsphere} + r \times N_{yi}$$

$$P_{zi} = C_{zlocalsphere} \times r \times N_{zi} \qquad (1)$$

Here, C represents the center of the sphere with a radius r, N is the vertex normal and P is the vertex position.

The local sphere fitting problem may be solved by calculating the center and radius if the local sphere in a linear least square fashion. The three equations may be expressed for each vertex in the one ring neighborhood of each vertex and a sphere center and radius may be assigned to these vertices. This linear least square system may be illustrated as the following matrix A of size 3n×4, where X is a 4×1 matrix and B is a 3n×1 matrix (where n is a number of neighbors in one ring neighborhood):

$$\underbrace{\begin{pmatrix} 1 & 0 & 0 & N_{x1} \\ 0 & 1 & 0 & N_{y1} \\ 0 & 0 & 1 & N_{z1} \\ \vdots & \vdots & \ddots & \vdots \\ 0 & 0 & 1 & N_{zn} \end{pmatrix}}_{A} \underbrace{\begin{pmatrix} Center_x \\ Center_y \\ Center_z \\ radius \end{pmatrix}}_{X} = \underbrace{\begin{pmatrix} P_{x1} \\ P_{y1} \\ P_{z1} \\ \vdots \\ P_{zn} \end{pmatrix}}_{B} \quad (2)$$

To solve this linear least square system, normal equations $(A^tA)X=A^tB$ and desired solution $X=(A^tA)^{-1}A^tB$ may be used. Upon finding the center and radius of the local sphere, an inflation force may be calculated based on the projection of each vertex on this local sphere. The following equations may be used for projection and inflation force calculations. Here the factor μ may affect the amount of inflation for each vertex. For example, satisfactory results may be obtained using an inflation of 2 percent. The user may, however, adjust this parameter ti increase the amount of inflation:

$$v_i^{n+1} w_{originalposition} \times v_i^n + w_{sphere} \times (Center+(radius+\mu) \times N_i) \quad (3)$$

$$Inflation(v_i)=(v_i^{n+1}-v_i^n) \quad (4)$$

Smoothing may be used to create high quality transitions between the edge and adjacent regions. The following equation may be used to calculate smoothing force and final additive blending force:

$$Smooth(v_i) = \sum_{j=0}^{n} \frac{1}{(\|v_j - v_i\|)} \times (v_i - v_j) \quad (5)$$

Additive blending may be used in addition to smoothing to remediate the sharp/concave edge within the region of interest. An additive blending tool used may be a combination of the local sphere fitting based inflation and vertex averaging based smoothing applied in an iterative manner. Moreover, inflation may be applied to concave vertices such as those vertices which move along the outward normal direction during inflation. Two weights may be used to balance the amount of forces acting on each vertex. The weight $w_{inflation}$ may be used to control the amount of inflation to expand concave vertices. The other weight $w_{smoothing}$ may be used to control the effect of smoothing. The following equation may be used to calculate the final additive blending force:

$$F_{blend}(v_i)=w_{smoothing} \times Smooth(v_i)+w_{inflation} \times Inflation(v_i) \quad (6)$$

After surface smoothing has been performed within the automatically identified region of interest (Step S26), the smoothed 3D polygon mesh model may be sent to a 3D printer 34 for 3D printing (Step S27).

Figure 5:
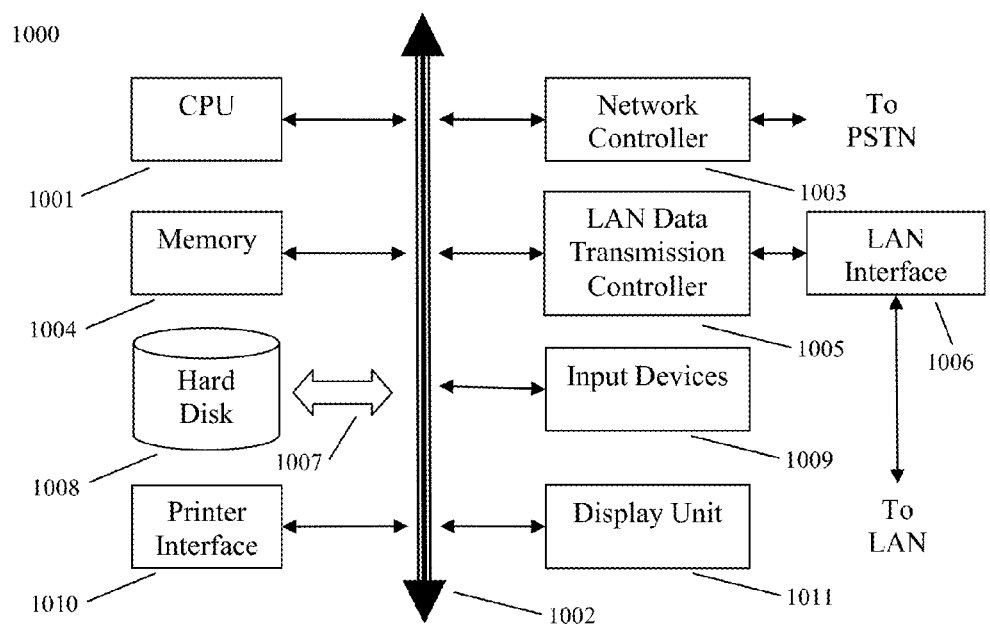
FIG. 5 shows an example of a computer system capable of implementing the method and apparatus according to embodiments of the present disclosure.

Administration of the above steps may be performed with the use of a computer system. The computer system may permit FIG. 5 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for designing a personalized medical device, comprising:
   receiving a template design of a medical device;
   acquiring an image including a patient anatomical geometry;
   combining the received template design of the medical device with the acquired image including the patient anatomical geometry to create a custom medical device design;
   displaying the combined image to a user;
   receiving, from the user, one or more seed points indicative of a location of a sharp concave edge present within the custom medical device design;
   automatically identifying, within the custom medical device design, a region of interest encompassing the sharp concave edge using the one or more seed points received from the user;
   performing surface smoothing of the custom medical device design within the region of interest to bolster a thickness of the custom medical device design within the region of interest; and
   obtaining a model from the surface smoothed custom medical device design.

2. The method of claim 1, wherein the received template design of the medical device is a three-dimensional polygonal mesh model.

3. The method of claim 1, wherein the received template design of the medical device is a computer aided design (CAD) model.

4. The method of claim 1, wherein a computed tomography (CT) scanner is used to acquire the image including the patient's anatomical geometry and the acquired image is a CT scan.

5. The method of claim 1, wherein one or more Boolean operators are used to combine the received template design of the medical device with the acquired image including the patient anatomical geometry.

6. The method of claim 1, wherein the user provides two seed points indicative of the location of the sharp concave edge including a first seed point located on one side of the sharp concave edge and a second seed point located on an opposite side of the sharp concave edge.

7. The method of claim 6, wherein automatically identifying the region of interest encompassing the sharp concave edge includes:
identifying shortest paths from the first seed point to a top and bottom boundary of the region of interest;
identifying shortest paths from the second seed point to a top and bottom boundary of the region of interest; and
identifying the region of interest as an area between the shortest paths of the first seed point and the shortest paths of the second seed point.

8. The method of claim 1, wherein after the region of interest is automatically identified, the user is provided with an opportunity to modify the region of interest either by adding/removing sections from the region of interest or by selecting one or more replacement seed points.

9. The method of claim 1, wherein performing surface smoothing of the custom medical device design within the region of interest includes performing one or more mesh fairing techniques.

10. The method of claim 1, wherein performing surface smoothing of the custom medical device design within the region of interest includes performing one or more edge blending techniques.

11. The method of claim 1, wherein performing surface smoothing of the custom medical device design within the region of interest includes performing one or more sphere fitting techniques.

12. The method of claim 1, wherein performing surface smoothing of the custom medical device design within the region of interest includes iteratively performing additive blending and sphere fitting.

13. The method of claim 1, wherein performing surface smoothing of the custom medical device design within the region of interest includes performing inflation of concave vertices.

14. The method of claim 1, wherein performing surface smoothing of the custom medical device design within the region of interest includes applying anisotropic discrete filter formulation that uses local principal curvature values to detect local sharp regions and utilizing a smoothing algorithm to apply different amounts of energy minimization to different local regions within the region of interest.

15. The method of claim 1, wherein performing surface smoothing of the custom medical device design within the region of interest includes performing mean curvature flow-based smoothing to preserve local features.

16. The method of claim 1, wherein performing surface smoothing of the custom medical device design within the region of interest includes applying bilateral filters to discrete surfaces of the custom medical device design to denoise surfaces thereof while preserving sharp features.

17. The method of claim 1, wherein the model obtained from the surface smoothed custom medical device design is a 3D-printable mesh model.

18. The method of claim 1, further including 3D printing the model obtained from the surface smoothed custom medical device design.

19. A method for fabricating a personalized medical device, comprising:
receiving a template design of a medical device;
acquiring an image including a patient anatomical geometry;
combining the received template design of the medical device with the acquired image including the patient anatomical geometry to create a custom medical device design;
identifying, within the custom medical device design, a region of interest encompassing a sharp concave edge using one or more seed points received from a user;
performing surface smoothing of the custom medical device design within the region of interest to bolster a thickness of the custom medical device design within the region of interest; and
three-dimensional (3D) printing the surface-smoothed custom medical device design.

20. A computer system comprising:
a processor; and
a non-transitory, tangible, program storage medium, readable by the computer system, embodying a program of instructions executable by the processor to perform method steps for designing a personalized medical device, the method comprising:
receiving a template design of a medical device;
acquiring an image including a patient anatomical geometry;
combining the received template design of the medical device with the acquired image including the patient anatomical geometry to create a custom medical device design;
identifying, within the custom medical device design, a region of interest encompassing a sharp concave edge using one or more seed points received from a user;
performing surface smoothing of the custom medical device design within the region of interest to bolster a thickness of the custom medical device design within the region of interest; and
three-dimensional (3D) printing the surface-smoothed custom medical device design.

* * * * *